United States Patent [19]
Davis et al.

[11] Patent Number: 6,008,052
[45] Date of Patent: Dec. 28, 1999

[54] PRESERVATION OF CELLS AS CONTROLS OR STANDARDS IN CELLULAR ANALYSIS

[75] Inventors: Kenneth A. Davis, Los Altos; Anthony J. Ward, San Ramon, both of Calif.

[73] Assignee: Becton, Dickinson & Company, Franklin Lakes, N.J.

[21] Appl. No.: 07/897,616

[22] Filed: Jun. 10, 1992

Related U.S. Application Data

[63] Continuation of application No. 07/556,934, Jul. 23, 1990, abandoned.

[51] Int. Cl.$^6$ ....................................................... C12N 5/08
[52] U.S. Cl. .............................. 436/10; 436/63; 436/172; 435/7.24
[58] Field of Search ..................... 436/8–18, 63, 436/172, 548; 435/7.24

[56] References Cited

U.S. PATENT DOCUMENTS

| | | | |
|---|---|---|---|
| 4,452,773 | 6/1984 | Molday | 436/529 |
| 4,489,162 | 12/1984 | Hawkins et al. | 436/10 |
| 4,731,330 | 3/1988 | Hill et al. | 436/10 |
| 4,777,139 | 10/1988 | Wong et al. | 436/10 |

FOREIGN PATENT DOCUMENTS 9004329  5/1990  WIPO .

OTHER PUBLICATIONS

Hess, A. "Calcium Inhibits Catecholamine Depletion By Reserpine From Carotid Body Glomus Cells." Brain Res Bull 1 (4.). 1976 359–362. Abstract, Biosys AN 78:116991.

Tischler, Arthur et al. "Morphologic and Cytochemical Properties of a Clonal Line of Rat Adrenal Pheochromocytoma Cells which Respond to Nerve Growth Factor." Laboratory Investigation 39(2). 1978 77–89.

Collins et. al., J. Histochemistry and Cytochemistry, 29, pp. 411–414 (1981).

*Primary Examiner*—Jill Warden
*Attorney, Agent, or Firm*—Susan A. Capello, Esq.

[57] ABSTRACT

Cells fixed with a fixative, reduced with a Schiff's base reducing agent and then dried in the presence of α-α-trehalose retain their light scatter and fluorescence properties and may be used, when rehydrated, as standards or controls in cellular analysis.

18 Claims, 15 Drawing Sheets

PRESERVATION OF CELLS AS CONTROLS OR STANDARDS IN CELLULAR ANALYSIS

This application is a continuation, of application Ser. No. 556,934, filed Jul. 23, 1990, now abandoned.

BACKGROUND OF THE INVENTION

This invention relates to the use of dried cells which can be stored, rehydrated and used as controls or standards, and in particular, relates to the use of mammalian cells fixed with a fixative, reduced with a Schiff's base reducing agent and then freeze-dried in the presence of trehalose which when rehydrated retain their light scatter properties and labelling properties when labelled with cell markers such that they can be used as standards or controls in cellular analysis such as flow cytometry and other forms of image analysis.

BACKGROUND OF THE INVENTION

Cellular analysis generally comprises the analysis of cells. This analysis can include visual inspection via light or fluorescent light microscopy and can further include automated analysis by means of image analysis and flow cytometry. In each instance, cells are stained with one or more labelled cell surface markers, fixed in a fixative and then examined. Examination of the cells and their markers can provide information regarding the lineage of the cell and/or its maturational stage.

In all forms of cellular analysis, including those described above, it is important in many instances to provide for controls and/or standards in order to ensure that the experimental or clinical results obtained are valid. For example, the procedures used to prepare specimens of cells are subject to a variety of conditions which can effect how the cell will be viewed during analysis. A control cell which has the properties expected from the specimens in the sample can provide a control or standard by which to confirm proper cell preparation. Controls and standards are particularly important in flow cytometry and image analysis.

Flow cytometry comprises a well known methodology for identifying and distinguishing between different cell types in a non-homogeneous sample. The sample may be drawn from a variety of sources such as blood, lymph, urine, or may be derived from suspensions of cells from hard tissues such as kidney or liver. In the flow cytometer, cells are passed substantially one at a time through one or more sensing regions where each cell is interrogated by an energy source. The energy source generally comprises means that emits light of a single wavelength such as that provided by a laser (e.g., He/Ne or argon) or a mercury arc lamp with appropriate filters.

In series with the sensing region, various light collection means, such as photomultiplier tubes, are used to gather light that passes through each cell (generally referred to as forward light scatter), light that is reflected orthogonal to the direction of the flow of the cells through the sensing region (generally referred to as orthogonal light scatter) and one or more light collection means to collect fluorescent light that may be emitted from the cell as it passes through the sensing region and is interrogated by the energy source.

Flow cytometers further comprise data recording and storage means, such as a computer, wherein separate channels record and store the light scattered and fluorescence emitted by each cell as it passes through the sensing region. By plotting orthogonal light scatter versus forward light scatter, one can distinguish between granulocytes, monocytes and lymphocytes in a population of leukocytes. By electronically (or manually) gating on only lymphocytes using light scatter, for example, and by the use of appropriate immunofluorescent markers, such as monoclonal antibodies labelled with fluorochromes of different emission wavelength, one can further distinguish between cell types within the lymphocyte population (e.g., between T helper cells and T cytotoxic cells). U.S. Pat. Nos. 4,727,020, 4,704,891 and 4,599,307 describe the arrangement of the various components that comprise a flow cytometer and also the general principles of its use.

There are a number of variables that may affect the use and operation of a flow cytometer. One variable relates to the measurement of light scattered by or fluorescence emitted from the cells that pass through the sensing region. Another variable may be in the method of sample preparation and in particular the method by which immunofluorescent markers are reacted with the cells in a sample. Unless the instrument is properly calibrated to record scattered and fluorescent light and/or unless the method of staining the cells with immunofluorescent markers is consistent, there can be no assurance that the data recorded can be relied upon from one experiment to the next or from one day to the next for any given instrument.

Presently, there exist methods which make use of both blank and fluorescently labelled microbeads which may be used to align and calibrate the fluorescent channels of a flow cytometer. For example, U.S. Pat. Nos. 4,774,189 and 4,767,206 describe a method for using such microbeads to calibrate a flow cytometer. While it is indicated in these patents that the microbeads should have the light scatter properties of the cells to be examined in a sample, because these beads consist of polymeric microparticles, they cannot truly duplicate the light scatter properties of the individual cells. Similarly, prelabelled microbeads cannot be used to determine whether the staining procedures are being appropriately carried out. Accordingly, the above-described microbeads provide only a limited ability to standardize the operation of a flow cytometer.

It would be preferable to align the light collection means in a flow cytometer using a standard that mimics the cells to be studied in a sample. For example, if one were examining normal human peripheral blood leukocytes, it would be desirable to have a standard comprised of such leukocytes and have a standard plot of light scatter obtained from such cells accompany the standard cells in order to check the alignment of a flow cytometer. It also would be desirable to have normal cells prestained with immunofluorescent markers as controls to determine if fluorescence parameters, such as sensitivity of the photomultiplier tube(s) and fluorescence compensation, have been correctly adjusted. In addition, it would be desirable to stain such normal cells with the immunofluorescent markers to be used in conjunction with the staining of a cell sample as a control and to compare the result obtained with a standard plot in order to determine if the method of staining were correct.

Flow cytometry, however, is not the only form of cellular analysis where such properties are desirable. Image analysis generally comprises an automated (or semi-automated) means by which cells prepared on a slide are examined. The means generally comprise high resolution optics which converts the optical image by a camera which, in turn, is connected to an analog to digital converter to digitize the image observed in a field on the slide and further includes logic means for pattern recognition of cells. The camera further can be used to detect fluorescence emissions when the cells have previously labelled with fluorescently labelled cell surface markers. One such system for image analysis is commercially available under the tradename CAS™ which is further generally described in U.S. Pat. No. 4,741,043. Another image system similar to this is described in U.S. Pat. No. 4,202,037.

In either form of image analysis, it would be desirable to provide control slides having cells deposited thereon which would be similar to those to be viewed in a sample both as a standard and as a procedural control. U.S. Pat. No. 4,741,043 describes a control slide of this make up and further describes how such a slide could be used. The patent does not describe, however, how the cells on the slide are prepared, and does not describe, therefore, whether such cells have the characteristics of the present invention.

In a further form of cellular analysis, blood (or other body fluid) samples can be prepared for manual visual or semi-automated viewing when collected in a capillary tube. This system, which is commercially available from Becton Dickinson and Company under the tradename QBC™ and which is further described in U.S. Pat. No. 4,190,328, generally comprises a capillary tube which contains a cylindrical mass having a specific gravity such that it will float in one of the cell layers when a blood sample drawn therein is separated by centrifugation. The mass is selected such that it will form a thin annular space in the tube into which the cells will be crowded, thus increasing the concentration of cells in a restricted area. The tube then is examined with the aid of either a microscope or automated reader.

The tube may include cell markers dried in the tube which then are rehydrated upon addition of the fluid sample. It would be desirable, however, to further provide tubes filled with dried cells which could be rehydrated in a buffer and then examined as controls or standards and compared with cells in a specimen.

Until the present invention, it was not thought possible to prepare standards or controls such as these. Principally, the difficulty resided in the fact that cells which could be used as a standard (e.g., a specific cell line) could not be dried and stored for later use without significantly disrupting the light scatter properties of the cell. It is known, for example, that upon air-drying or freeze-drying that water in the lipid membrane of a cell and/or within the cell's organelles will cause the membranes to be disrupted upon drying, thus causing a significant alteration in the light scatter properties of the cell.

Previously, it also was widely believed that if the cells were fixed with a fixative agent (e.g., paraformaldehyde) before the cells were dried, some of the light scatter properties of the cells would be preserved, but it would not be possible to label the cells with a cell surface marker, such as an immunofluorescent marker after fixation. Thus, it was thought that it would not be possible to use such cells as a control for determining proper immunofluorescent staining procedures. While "fresh" cells might avoid each of these limitations, the ability to store and maintain such cells among the many persons practicing cellular analysis is not practical.

The present invention allows cells to be dried while retaining their light scatter properties and further allows the cells to be stained either before or after drying without losing their fluorescent properties. Accordingly, it is desirable to have dried cells that retain light scatter properties and also retain the ability to be tagged with cell surface markers.

A problem encountered through the use of any cells that have been fixed, however, is that autofluorescence of the cells increases with time. Autofluorescence is a property of most mammalian cells and is believed to be due to the presence of pyridine and flavin molecules which, respectively, impart UV-excited blue and blue-excited green fluorescence to cells. The amount of autofluorescence from unstained cells can be so great as to mask the measurement of weak fluorescent signals (e.g., cells labelled with fluorescein labelled monoclonal antibodies). As a result, before the present invention, cells increased in autofluorescence with time hence masking the fluorescent emmission(s) from the fluorescent marker(s). In the present invention, it has been suprisingly found that by reducing the cells with a reducing agent for Schiff's bases after fixation but before drying not only maintains the light scatter properties of the cell but suprisingly maintains Ad autofluorescence at essentially background levels without affecting any other properties of such cells.

SUMMARY OF THE INVENTION

The present invention comprises a cell which has been fixed, reduced and then dried in the presence of a protein, membrane stabilizing compound which preserves the light scattering properties of the cell and preserves the ability of the cell to be tagged with cell markers upon rehydration. The cells useful in this invention may be derived from any source including normal blood, bone marrow, lymph or solid tissues or may be derived from abnormal tissues such as leukemias or solid tissue cancers. The cells further may be provided already having been tagged with one or more markers prior to drying.

The present invention further provides a method for preparing cells which retain their light scatter properties and their ability to be tagged with cell markers wherein the method comprises 1) fixing the cells with a fixative, 2) reducing the cells with a reducing agent for Schiff's bases, such as cyanoborohydride, 3) mixing the cells with a protein, membrane stabilizing compound in sufficient quantity to prevent denaturization of the proteins and other macromolecules that comprise the cell and to preserve the light scatter properties and ability to be stained with such markers and 4) drying the cells. In this method, the cells may be dried at a temperature above or below the freezing point of water. The cells also may be dried at a pressure above or below atmospheric. It is preferable to freeze-dry (or lyopholize) the cells.

The cell markers that may used in the practice of this invention generally comprise any label that reacts with a structure on the surface of or inside the cell. Such markers generally comprise antibodies (either polyclonal or monoclonal), preferably the antibodies are monoclonal. The markers may be tagged with a stain that provides for visualization of the marker. Examples of such stains include fluorescent dyes (e.g., phycobiliproteins, fluorescein, rhodamine or cyanine dyes), radio-isotopes, liposomes (which may have fluorescent dyes incorporated therein) and enzymes (which will catalyze a color forming or color eliminating reaction). The specific combination of a monoclonal antibody and fluorescent dye comprises an immunofluorescent marker. The choice of marker and the stain attached thereto is not critical to the practice of this invention. It also should be appreciated that cells markers may further include nucleic acid stains, such as those described in U.S. Pat. No. 4,544,546, and more particularly stains of the type described by formula III therein.

The present invention further comprises a method and kit to calibrate a flow cytometer which comprises rehydrating the fixed, dried cells of the present invention, running the cells through a flow cytometer and comparing the light scattering results attained with those provided as a standard plot. In this embodiment of the invention, the dried cells may also be labelled with one or more cell markers. If the cells are labelled, the fluorescence channels also may be calibrated.

Labelled cells also may be used as a control for calibration and compensation of an instrument calibrated with a microbead standard as described above.

The present invention still further comprises a method and kit comprising control cells for fluorescent staining procedures whereby a cell is fixed, reduced and then dried with a protein, membrane stabilizing compound, is rehydrated and then stained with one or more cell markers, run through a flow cytometer and the fluorescence emission(s) recorded is compared with a fluorescence standard plot.

The present invention also comprises a control slide kit for image analysis comprising cells which have been fixed, reduced and then dried onto a slide or into a capillary tube with a protein, membrane stabilizing compound. The slide then may be examined upon rehydration.

DETAILED DESCRIPTION OF THE INVENTION

Figure 1A:
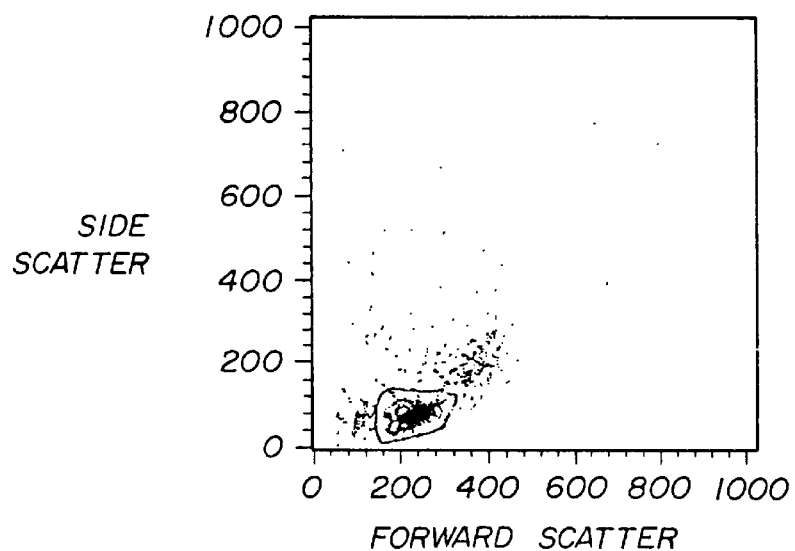
FIG. 1 comprises several plots of orthogonal light scatter vs. forward light scatter (A,B) for normal peripheral blood mononuclear cells stained with Anti-Leu 2a (PE) and Anti-Leu 3a (FITC), with a gate drawn around the lymphocyte population, and plots of log fluorescence (C,D) for the gated population wherein the cells were stained and examined without fixation (A,C) or were fixed in 0.1% paraformaldehyde, freeze-dried in a solution of PBS containing a 10% trehalose, rehydrated and then stained (B,D).

In one embodiment of the present invention, cells are fixed with a fixative, such as paraformaldehyde, reduced in the presence of a Schiff's base reducing agent, such as cyanoborohydride, stained with one or more cell markers, dried in the presence of a protein, membrane stabilizing compound for use as a control or standard in cellular analysis. In another embodiment of the present invention, cells are fixed in the presence of a fixative, such as paraformaldehyde, reduced in the presence of a Schiff's base reducing agent, such as cyanoborohydride, dried in the presence of a protein, membrane stabilizing compound, rehydrated and then labelled with one or more cell markers as a control for sample staining procedures in cellular analysis. In both embodiments, surprisingly, upon rehydration, the cells retain their light scatter properties without an increase in autofluorescence, and in the second embodiment, retain their ability to react with cell markers. These properties are critical to their intended use.

The types of cells that can be dried and used as standards or controls should be similar, if not identical to, the cells expected to be present in samples to be later analyzed. Preferably, the cells to be dried comprise leukocytes and more preferably comprise one or more subsets thereof such as peripheral blood mononuclear cells ("PBMC"). In another embodiment, one or more leukocytes subsets, such as lymphocytes, monocytes and/or granulocytes (or further subsets of each), may be used. Leukocytes, and subsets thereof, may be derived from normal healthy donors that may be separated from erythrocytes by means of lysis and/or density dependent centrifugation or may be derived from normal cell lines established by the user or by a cell line depository such as the American Type Culture Collection, Rockville, Md. ("ATCC").

If the cells in a sample are believed to be abnormal, the cells to be dried as standards or controls may be derived from abnormal donors or, more appropriately, may be derived from a variety of abnormal cell lines. A number of human and other species tumor cell lines have been deposited with the ATCC and may be obtained from them. Cells from these tumor cell lines may then be dried as standards or controls.

The selection of the stabilizing compound is dependent upon its ability to protect proteins and membranes of the cell from denaturization and to preserve the light scatter properties of the cell as well as to preserve the ability of the cell to react with cell markers upon rehydration. A number of such compounds exist and have been described for the preservation of a number of substances including tumor necrosis factor (U.S. Pat. No. 4,457,916), meningococcal-capsule polysaccharides (U.S. Pat. No. 4,206,200), heat-killed viruses (EPA 86116691.6), "proteins or other macromolecules, such as enzymes, antibodies, antigens, serum complement, fluorescent proteins, vaccine components and polysaccharides" (U.S. Pat. No. 4,891,319) and antigen or antibody labelled polystyrene beads (GB 2016687B). Generally, a number of compounds have been tried by others and the group comprising mono-, di- and polysaccharides most often were used. In particular, the disaccharide α-α-trehalose was preferred.

Trehalose is a naturally occurring disaccharide which may be obtained from Baker's yeast. See Stewart et al., J. Am. Chem. Soc., 72:2059 (1950). Trehalose is known, in nature, to protect the lipid membranes and cell organelles of a variety of species such as yeast and brine shrimp from denaturation during periods of desiccation. Generally, trehalose may comprise up to 20% (w/v) of a cell. In the references presented above and in particular in U.S. Pat. No. 4,891,319, a percentage from between 0.05 to 20% by weight of trehalose and more particularly a ratio of trehalose to protein of 1.4:1 by weight is preferred and appears sufficient to prevent denaturation.

The cells may be dried after fixation and reduction but before labelling with cell surface markers or may be labelled after fixation and reduction but prior to drying. The selection of when the cells are labelled will depend upon the method of use.

Accordingly, in one preferred embodiment of this invention, PBMC are obtained from healthy donors and separated from whole blood by means of density dependent centrifugation. The resulting PBMC are fixed in paraformaldehyde, reduced with cyanoborohydride and then mixed with a solution containing between 1% and 20% (w/v) trehalose and more preferably 5%. The resulting mixture then is dried. While the majority of the above references recite that drying may occur below the freezing point of water, U.S. Pat. No. 4,891,319 further discloses that drying may occur above the freezing point of water. It is preferred that drying be done below the freezing point of water.

In order to illustrate the above embodiment of the invention, the following examples are provided. Referring to FIG. 1, PBMC were obtained by Ficoll-Hypaque density-dependent centrifugation of blood from normal donors.

Figure 1B:
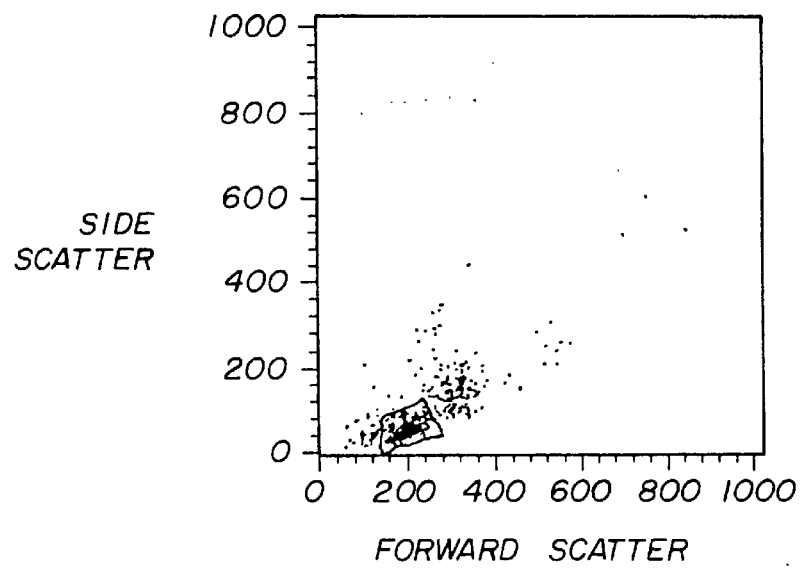
Figure 1C:
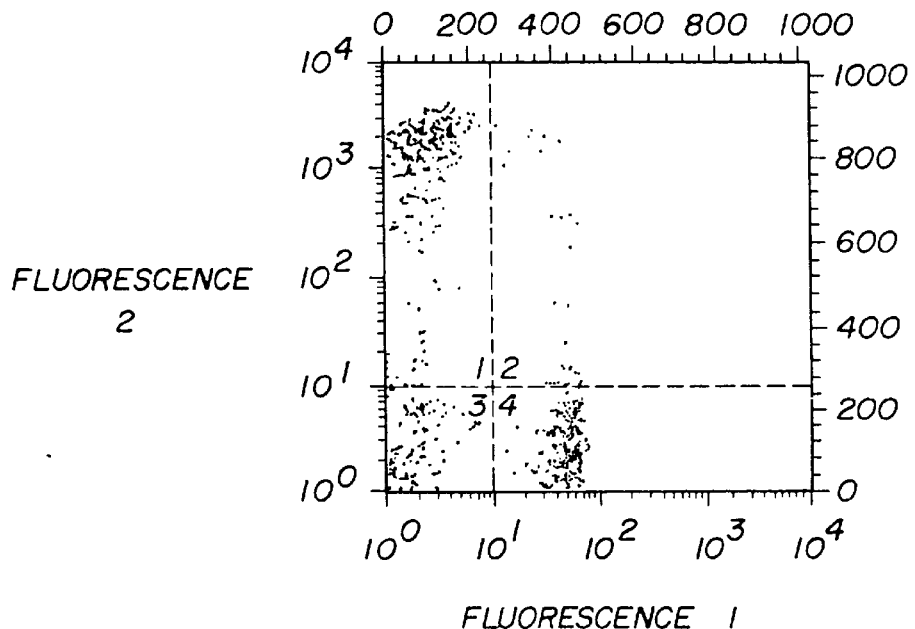
Figure 1D:
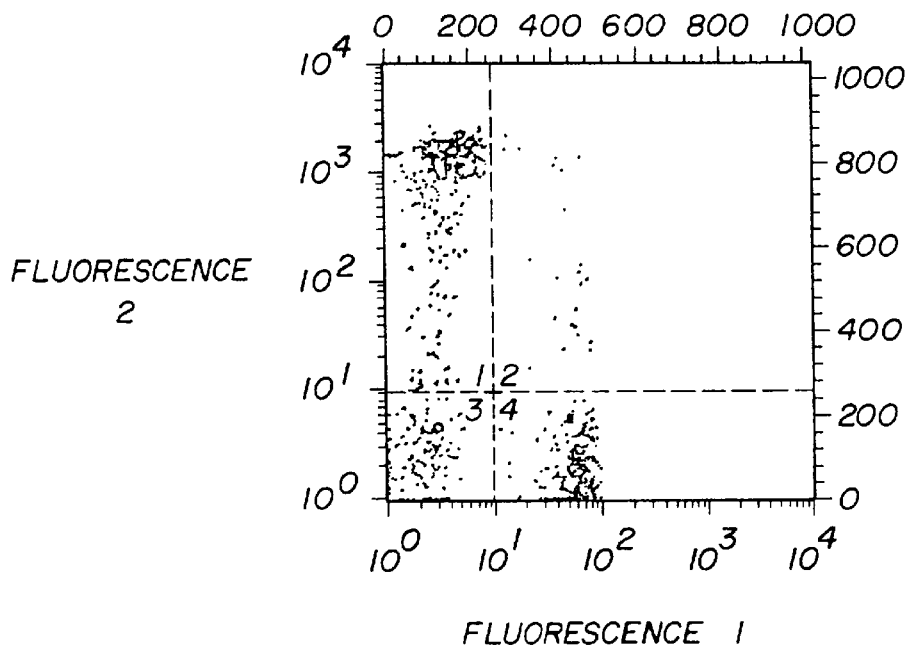
Figure 2A:
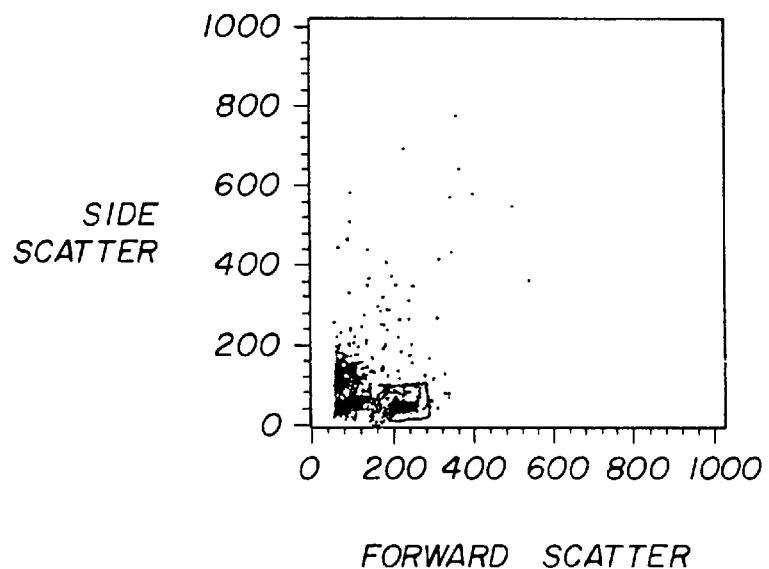
FIG. 2 comprises four plots of orthogonal light scatter and forward light scatter for normal peripheral blood mononuclear cells fixed in 0.5% paraformaldehyde and either air dried at 37° C. (A,B) or freeze-dried (C,D) in a solution of phosphate buffered saline (A,C) or 10% trehalose (B,D).
Figure 2B:
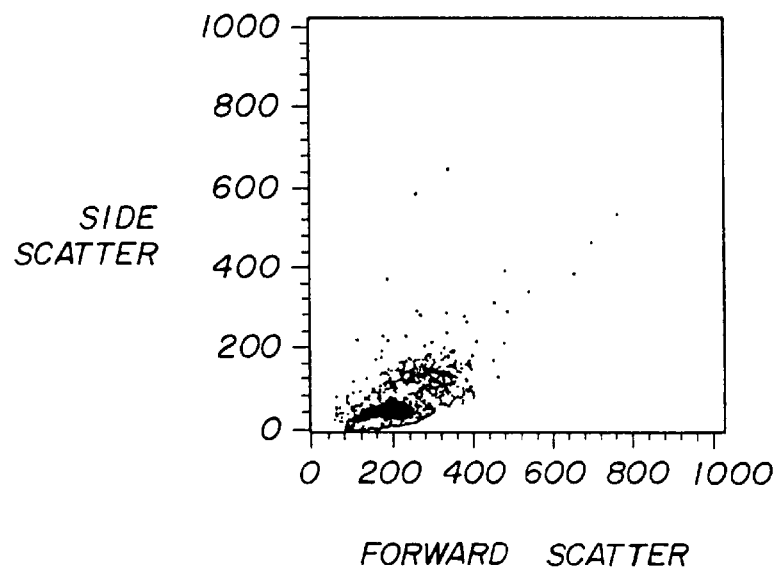
Figure 2C:
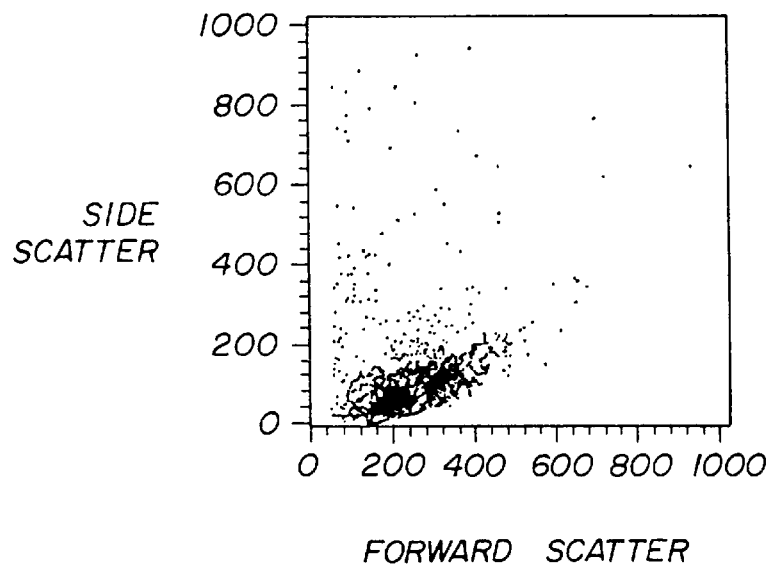
Figure 2D:
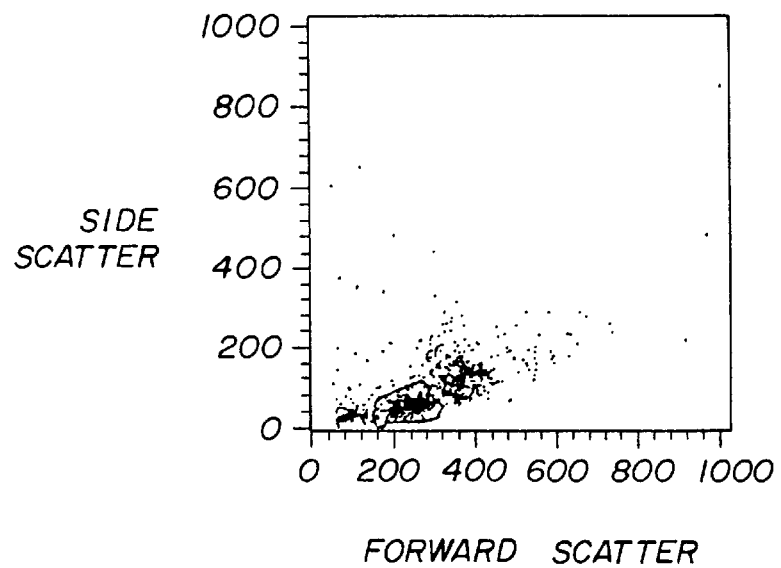

For FIGS. 1A and 1C, two monoclonal antibodies, Anti-Leu 3a and Anti-Leu 2a (Becton Dickinson Immunocytometry Systems) were conjugated to the fluorochromes fluorescein isothiocyanate ("FITC") and r-Phycoerythrin ("PE") respectively. Each of these labelled antibodies were added to the PBMC (in phosphate buffered saline ("PBS") and 0.5% bovine serum albumin ("BSA")) for a period of 20 minutes and then washed with PBS and 0.1% BSA.

Referring to FIGS. 1B and 1C, PBMC were fixed in a solution of 0.1% paraformaldehyde for 18 hours at 4° C. After fixation, the cells were washed twice in PBS and 0.1% BSA and a 10% solution (w/v) of trehalose in PBS was added. The cells in solution were freeze-dried in 12×75 mm polystyrene tubes. the cells were rehydrated in a solution of PBS plus 0.1% BSA for approximately 5 minutes. The cells then were stained with the immunofluorescence markers as above. All freeze-dried cells were stored at 4° C. over a dessicant. Regardless of the timing of staining, PBMC then were run through a Becton Dickinson Immunocytometry Systems FACScan™ flow cytometer equipped with Consort 30™ and Research Software. Data was acquired in list mode and stored for subsequent re-analysis. Similar procedures were used for other cell lines.

Referring to FIG. 1, orthogonal light scatter is plotted against forward light scatter for PBMC stained and unfixed (A,C) or fixed, freeze-dried in the presence of trehalose. As can be seen by comparing FIGS. 1A and 1B, the light scatter properties of the two different preparations do not significantly differ. Accordingly, the presence of trehalose in the sample does not effect the light scatter properties of the cells. Using the lymphocyte gate drawn, the fluorescence of the lymphocyte populations is shown in FIGS. 1C and 1D. As can be seen, fluorescence does not change even when staining occurs after fixation and drying.

Referring to FIG. 2, the effects of air drying verus freeze-drying on normal PBMC is seen for cells dried in the presence of a solution of PBS or PBS containing 10% trehalose. Comparing FIGS. 2A with 2C and 2B with 2D, it can be seen that light scatter properties of the cells change, particularly with respect to forward scatter. Comparing FIGS. 2A with 2B and 2C with 2D, it can be seen that light scatter again changes between PBS and trehalose, albeit less than that observed between air-drying and freeze-drying. Freeze-drying in the presence of trehalose is preferred, however.

Figure 3A:
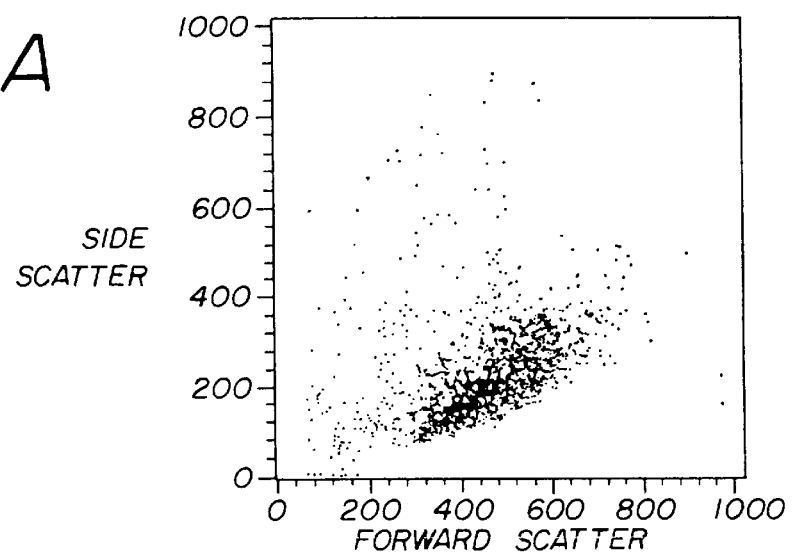
FIG. 3 comprises three plots of orthogonal light scatter vs. forward light scatter for HPB-ALL cells fixed in 0.1% paraformaldehyde and examined (A) or fixed and then freeze-dried in a solution of phosphate buffered saline (B) or 10% trehalose (C).
Figure 3B:
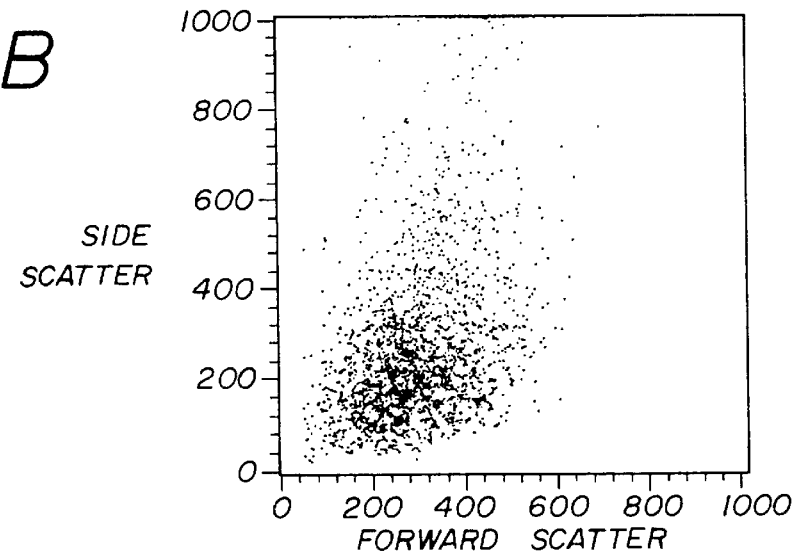
Figure 3C:
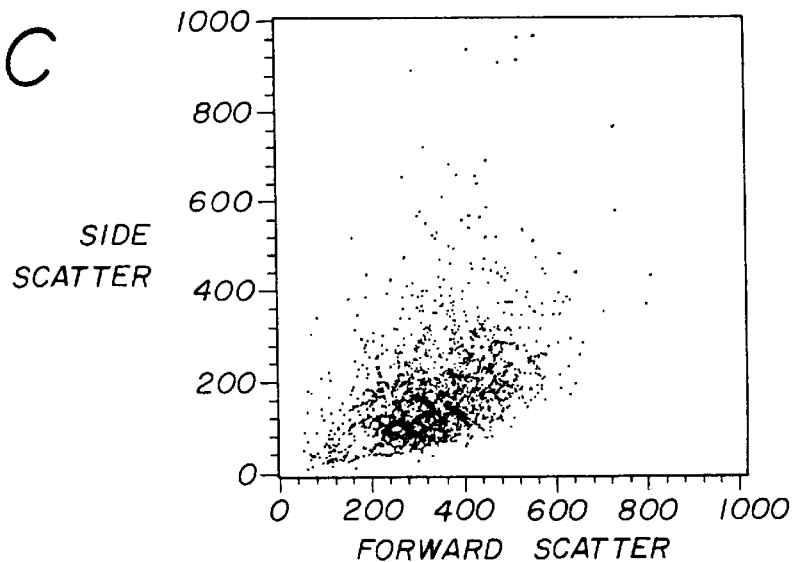

Referring to FIG. 3, HPB-ALL cells (a human T cell lymphoma line) were fixed in 0.1% paraformaldehyde and examined directly (A) or after freeze-drying in a solution of PBS (B) or PBS containing 10% trehalose (C) and rehydration. As in FIG. 2, the light scatter properties of cells dried in trehalose are superior to the light scatter properties of cells dried in PBS alone (i.e., FIG. 3C is more like FIG. 3A than FIG. 3B is like FIG. 3A).

Figure 4A:
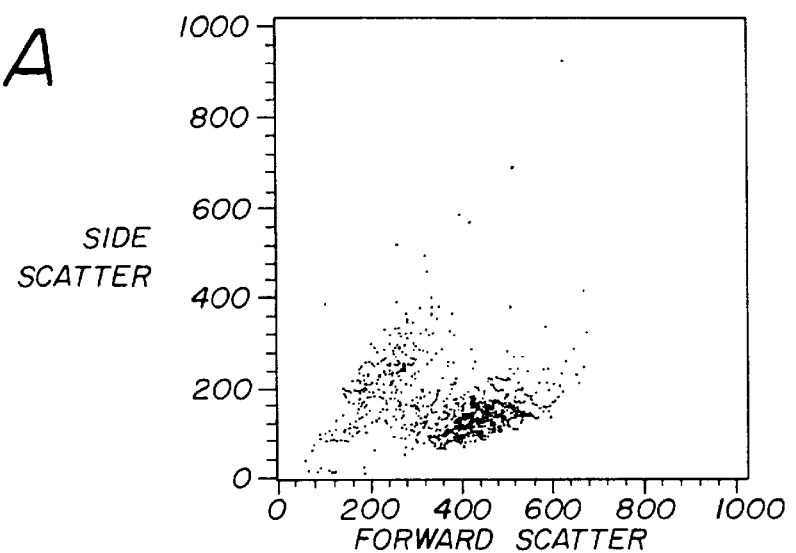
FIG. 4 comprises three plots of orthogonal light scatter versus forward light scatter for C6VL.1 cells freshly prepared (A) or freeze-dried in phosphate buffered saline (B) or in 10% trehalose (C).
Figure 4B:
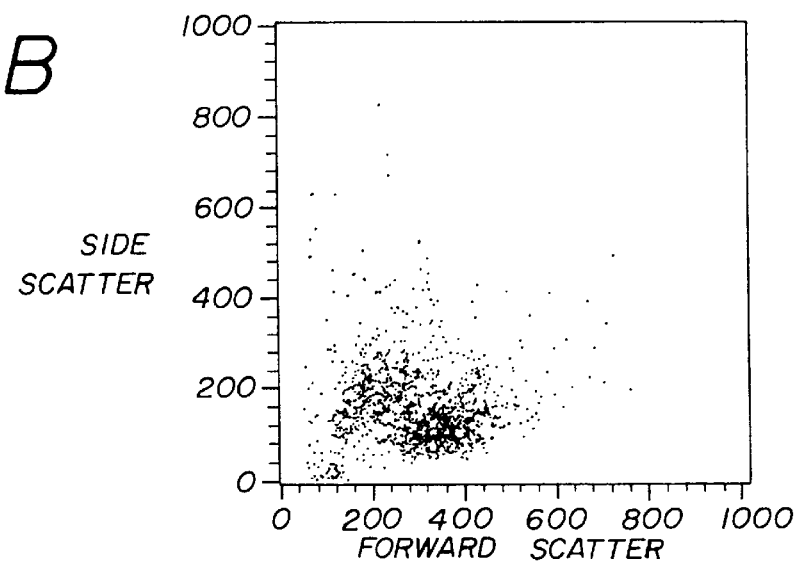
Figure 4C:
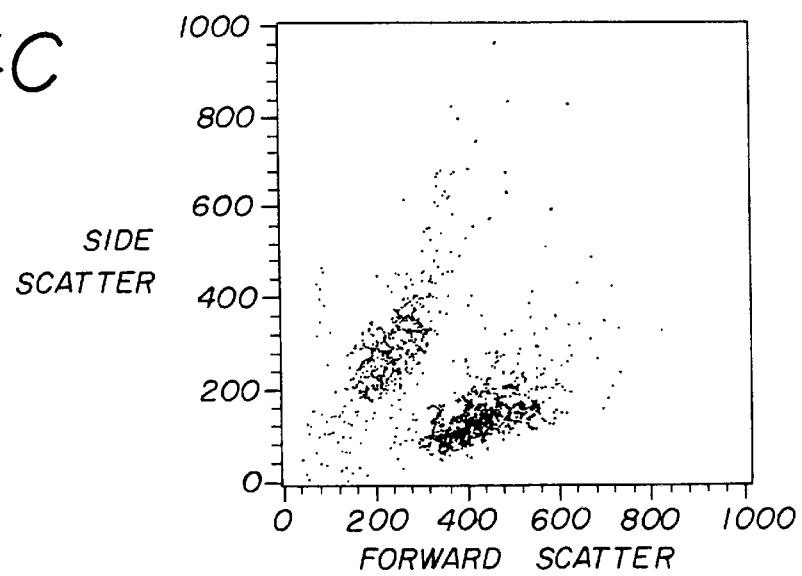
Figure 5A:
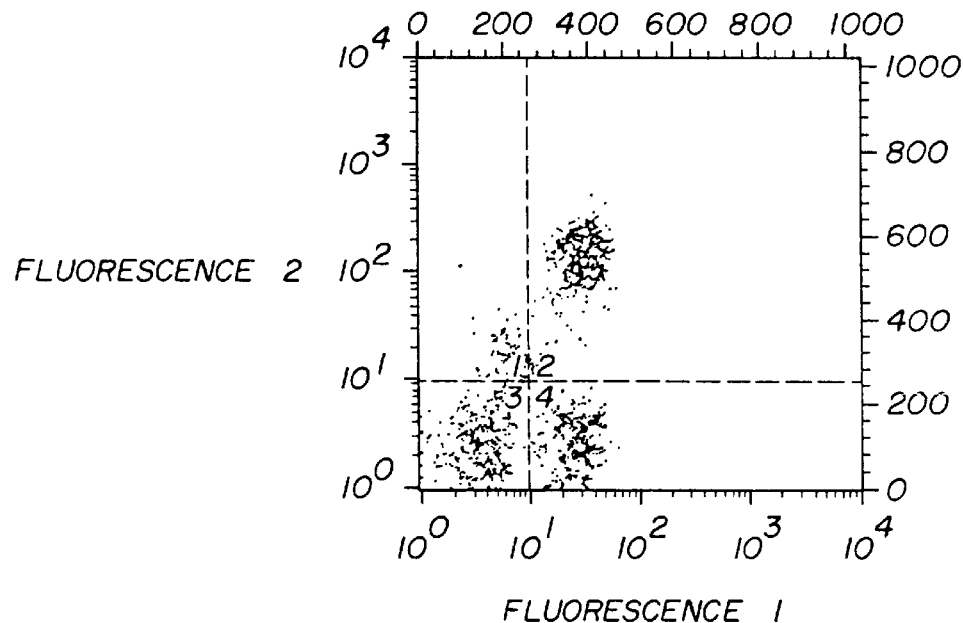
FIG. 5 comprises several plots of log mean fluorescence for peripheral blood mononuclear cells, gated for the lymphocyte population, fixed in 0.5% paraformaldehyde, reduced in 0.2 mg/ml cyanoborohydride, stained with Anti-Leu 4 (FITC) and Anti-Leu 3a (PE) and examined directly (A) or then freeze-dried in a solution containing 10% trehalose and stored at 4° C. for 4 days (B), 49 days (C) or 102 days (D) prior to rehydration and examination.
Figure 5B:
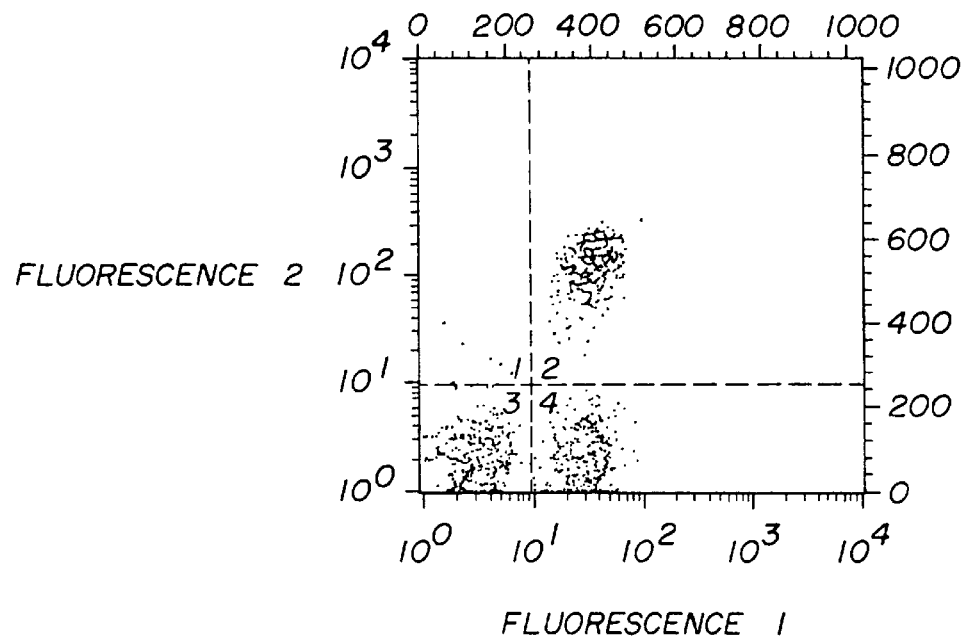
Figure 5C:
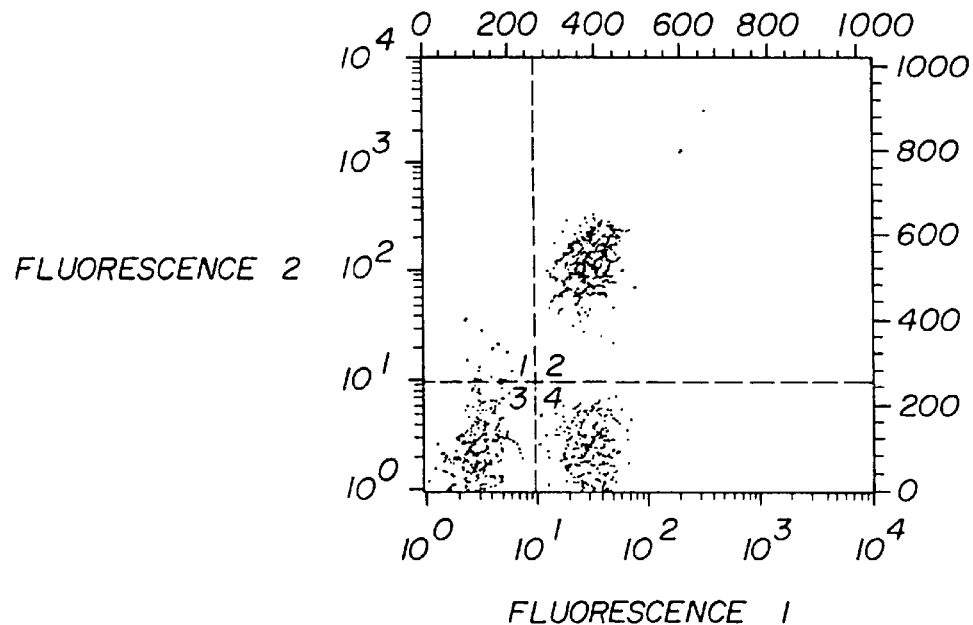
Figure 5D:
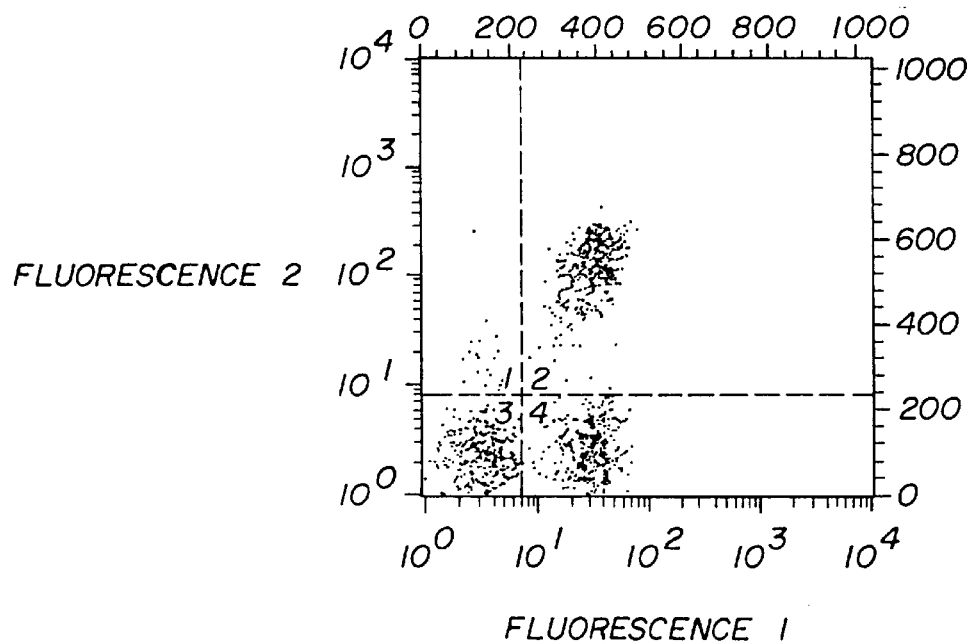
Figure 6A:
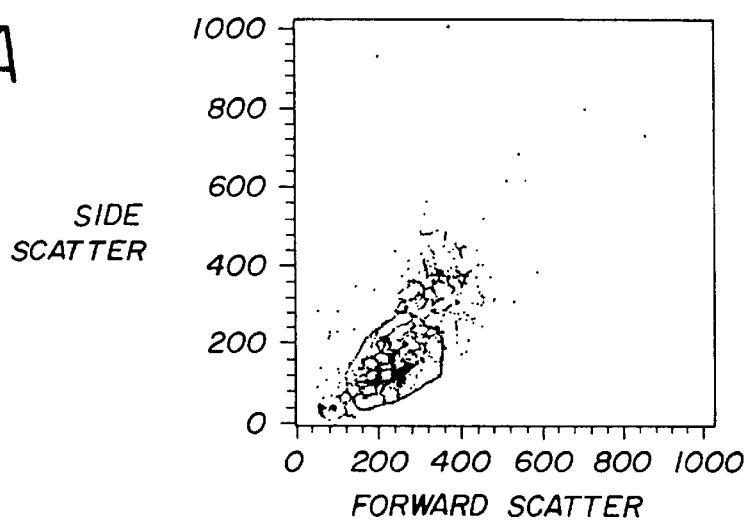
FIG. 6 comprises several plots of orthogonal light scatter versus forward light scatter for peripheral blood mononuclear cells fixed with 0.5% paraformaldehyde, reduced in 0.2 mg/ml of cyanoborohydride (A–D) or non-reduced (E–H) and freeze-dried in a solution of phosphate buffered saline containing 10% trehalose when measured over time.
Figure 6B:
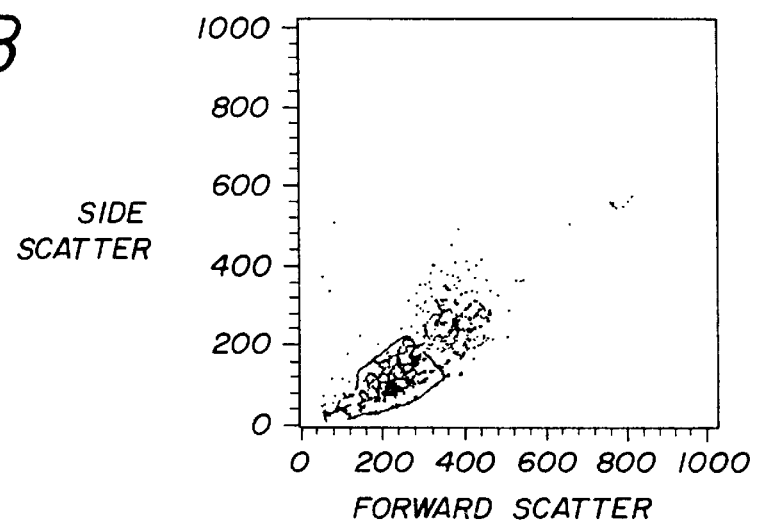
Figure 6C:
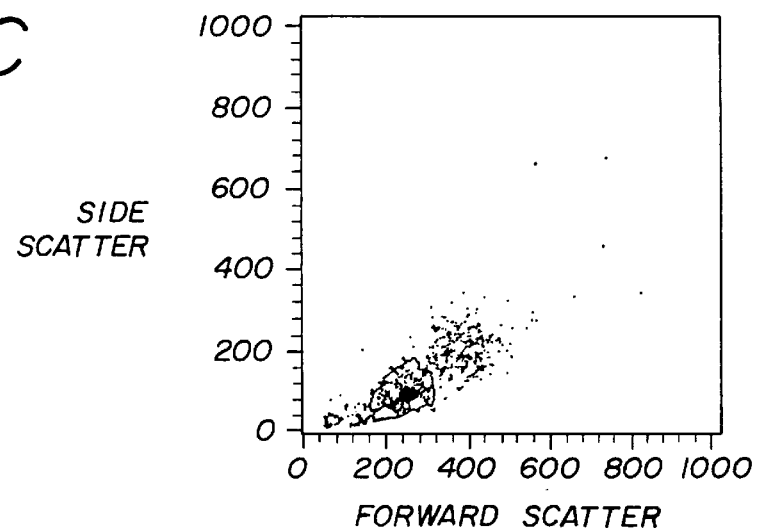
Figure 6D:
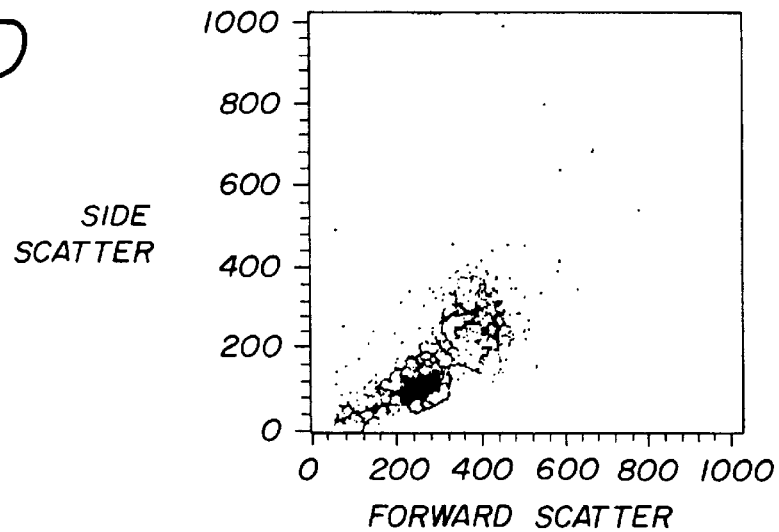
Figure 6E:
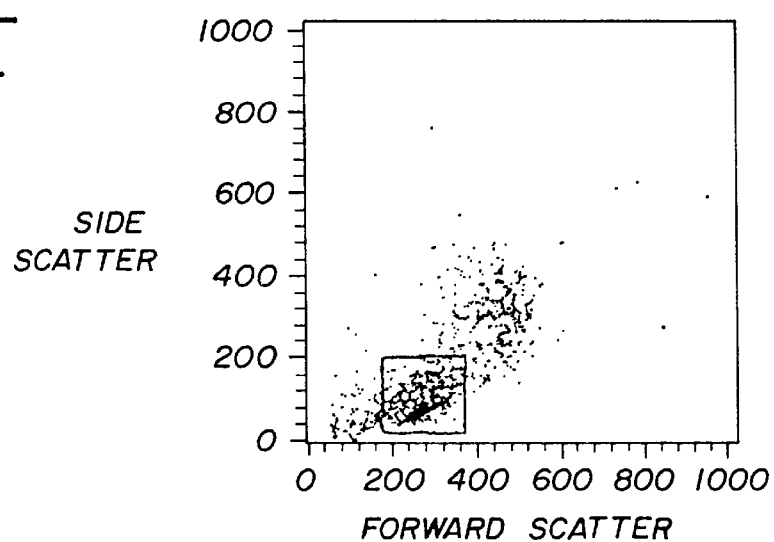
Figure 6F:
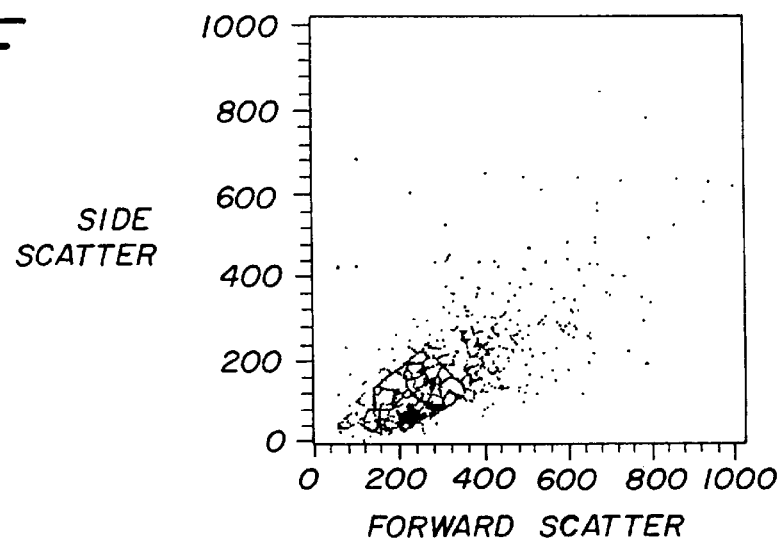
Figure 6G:
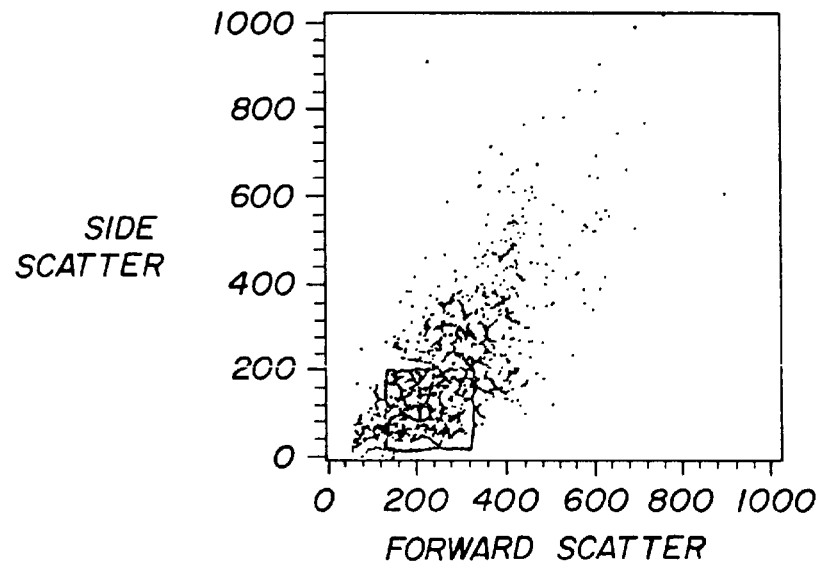
Figure 6H:
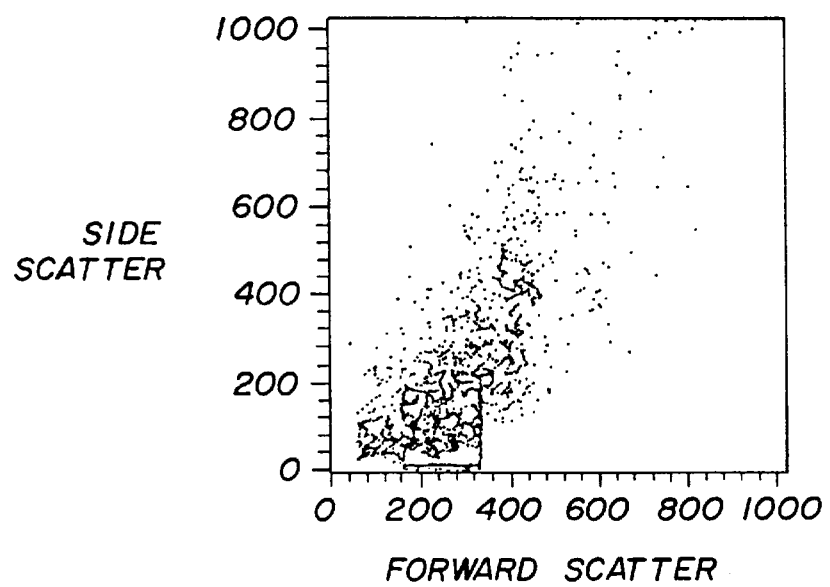
Figure 7A:
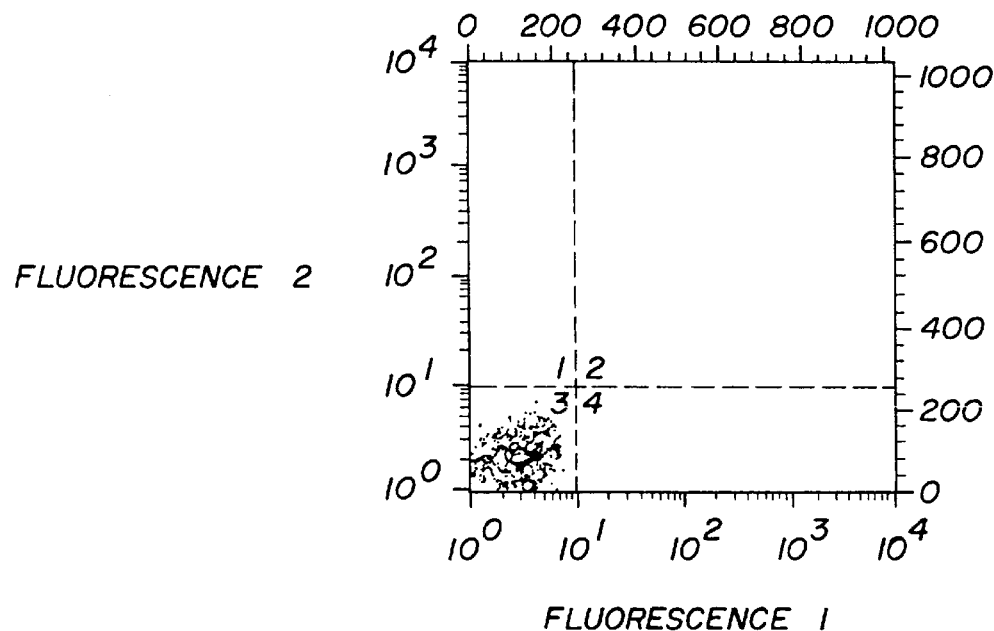
FIG. 7 comprises several plots of autofluorescence for peripheral blood mononuclear cells, gated on the lymphocyte population, fixed with 0.5% paraformaldehyde, reduced in 0.2 mg/ml of cyanoborohydride (A–D) or non-reduced (E–H) and freeze-dried in a solution of phosphate buffered saline containing 10% trehalose when measured over time.
Figure 7B:
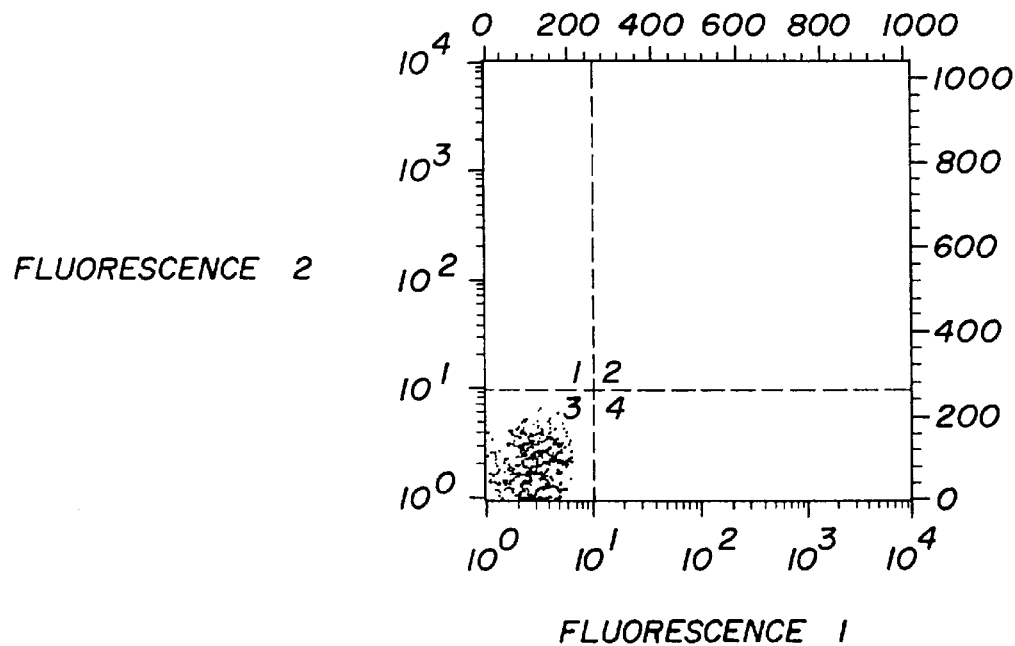
Figure 7C:
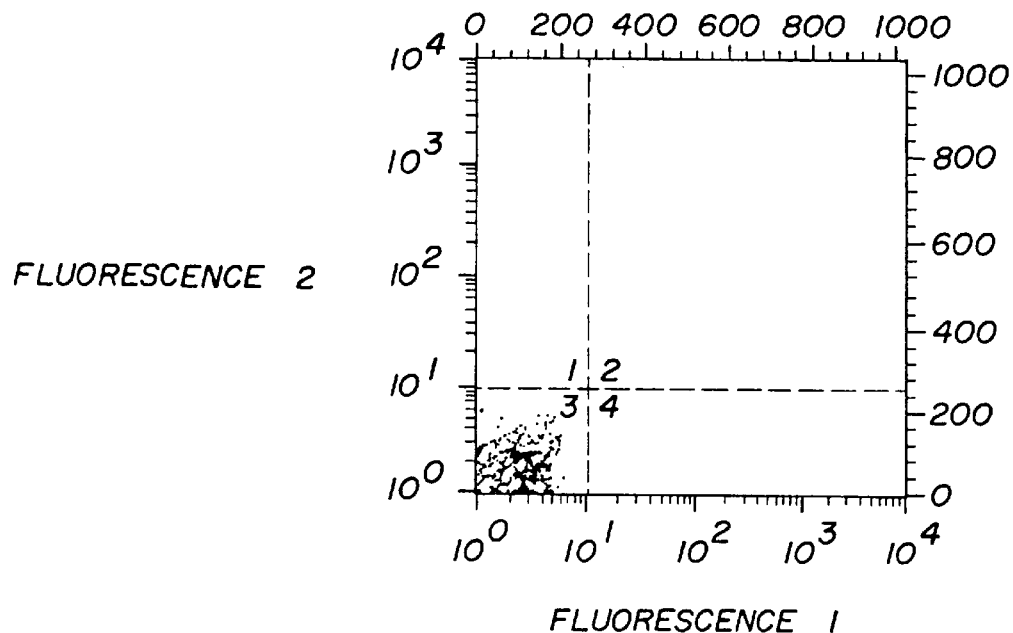
Figure 7D:
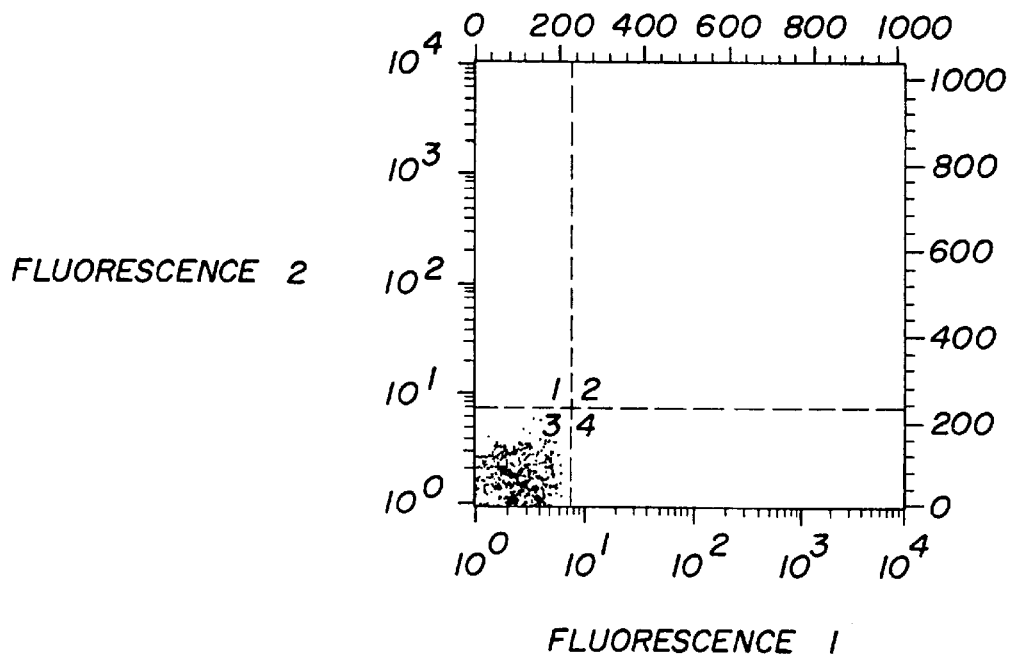
Figure 7E:
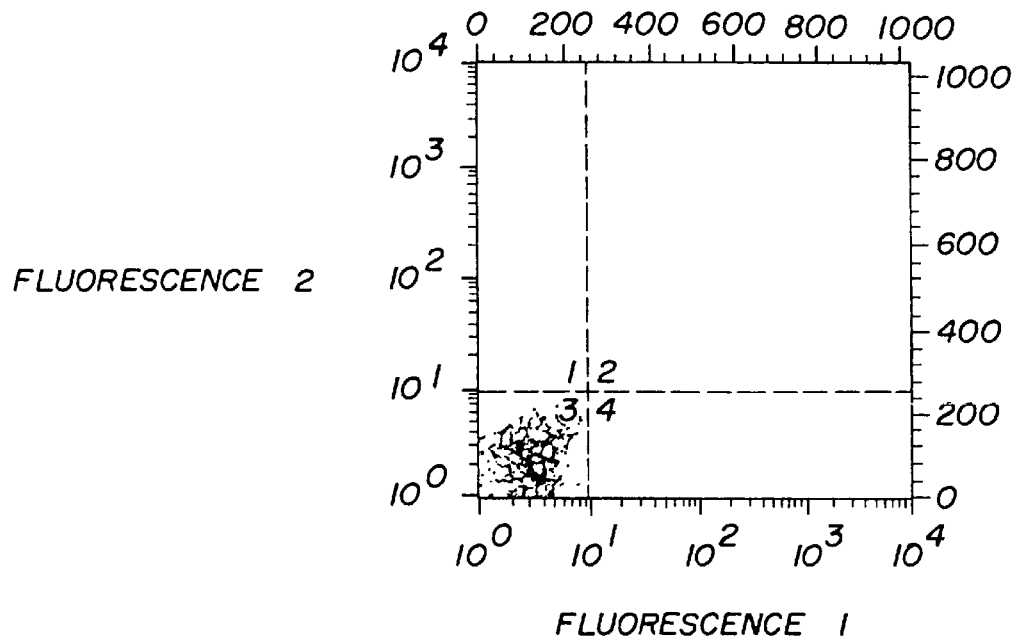
Figure 7F:
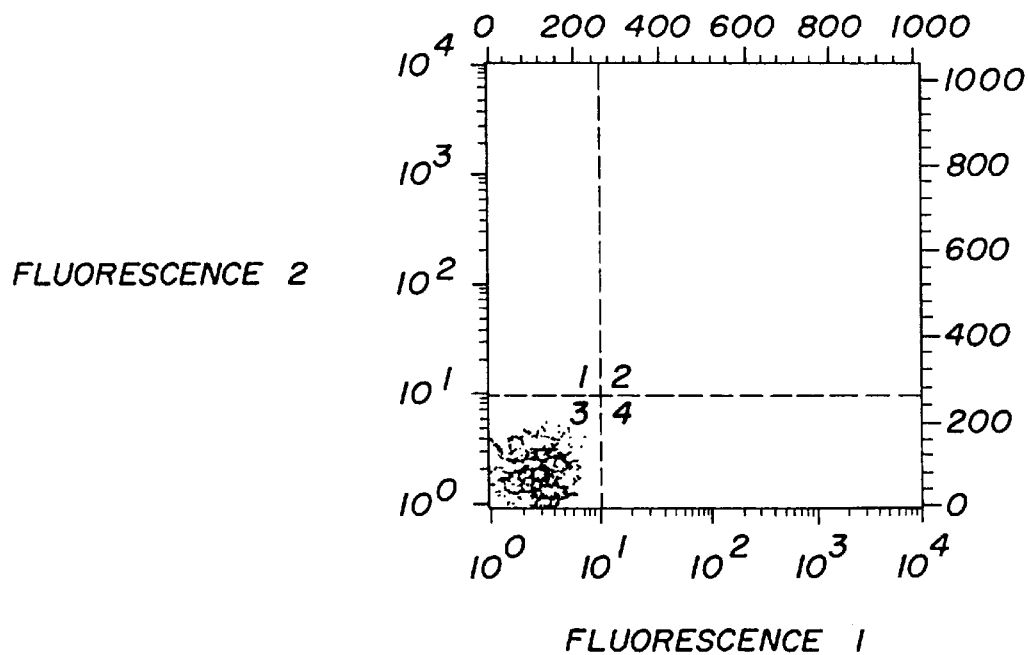
Figure 7G:
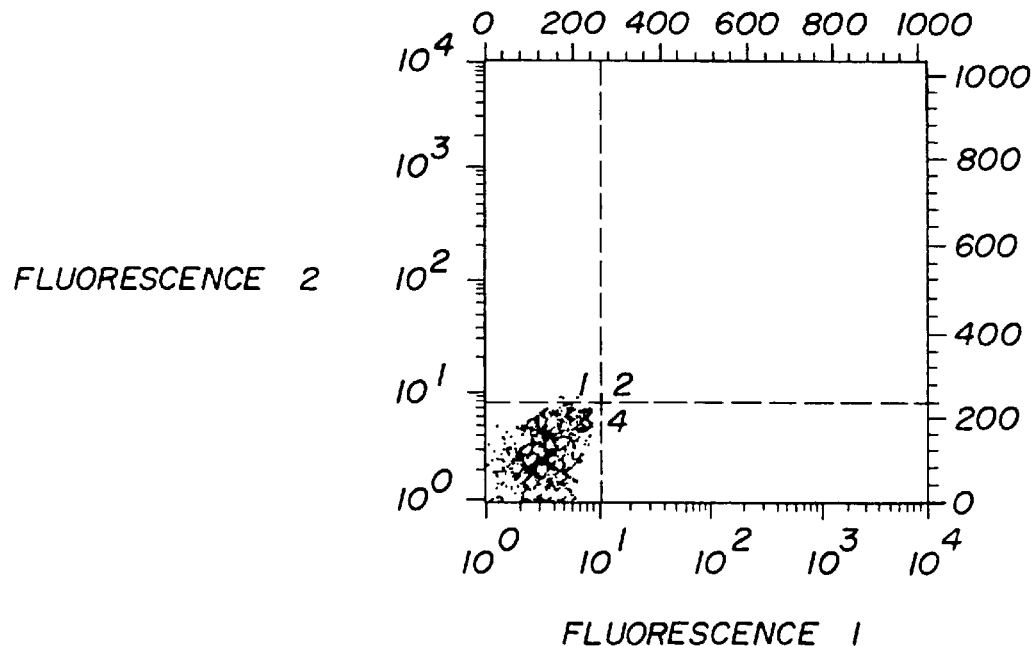
Figure 7H:
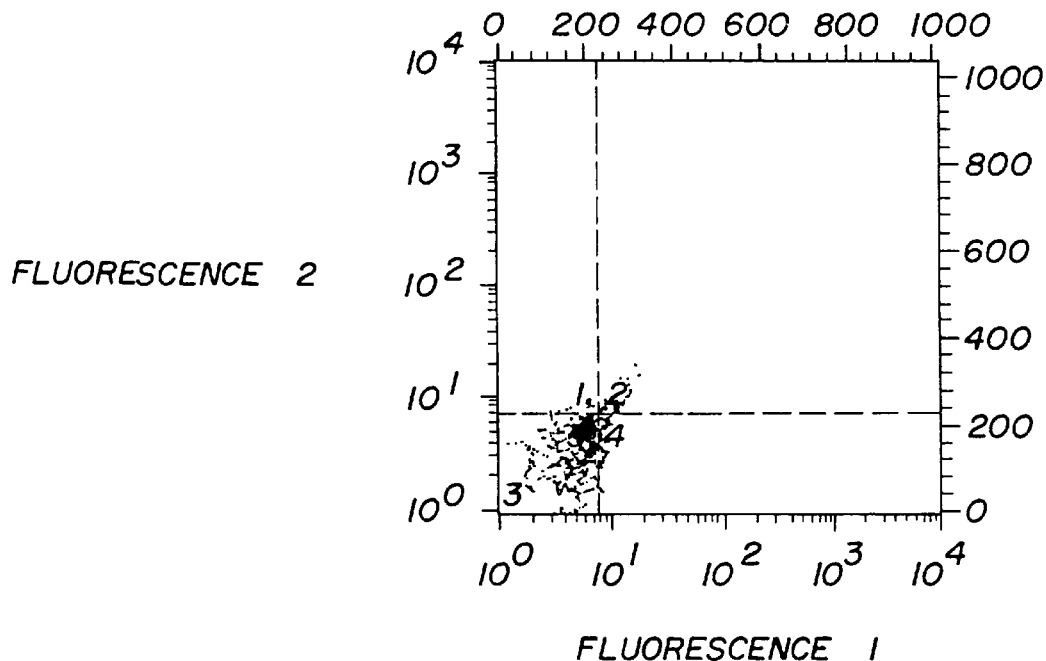

FIG. 4 comprises several plots of light scatter for unstained C6VL.1 cells (a mouse cell thymoma line) which have been fixed prior to analysis (A) or which have been fixed and then freeze-dried in the presence of PBS alone (B) or PBS and 10% trehalose (C). In this figure, it can be seen that the light scatter properties of the cells freeze-dried with trehalose are substantially the same as those from the freshly prepared cells. The cells freeze-dried in PBS alone do not maintain their scatter properties.

The ability of a stabilizing compound to preserve the properties of a labelled cell is set forth in FIG. 5. PBMC were fixed in 0.5% paraformaldehyde, reduced with 0.2 mg/ml of cyanoborohydride, stained with Anti-Leu 4 (FITC) and Anti-Leu 3a (PE) and then examined directly (A) or after freeze-drying, storage at 4° C. and rehydration. The freeze-dried cells were stored with a dessicant (to prevent atmospheric moisture from rehydrating the cells) and fluorescence was measured over a period of 102 days. As seen in FIG. 5, there is little or no detectable decrease in fluorescence with time, thus demonstrating the ability of the compound to preserve fluorescence.

Referring to FIGS. 6 and 7, the reduction of fixed cells prior to drying in order to stabilize scatter characteristics and minimize autofluorescence is shown. PBMC were fixed in 0.5% paraformaldehyde for 18 hours and then reduced with 0.2 mg/ml of cyanoborohydride for 24 hours (A–D). Other cells (E–H) were fixed but not reduced. The cells then were freeze-dried in a solution of PBS containing 10% (w/v) of trehalose, with the exception of (A) and (E) which were analyzed without having been freeze-dried. All cells, except (A) and (E), were stored at 4° C. in the presence of a dessicant.

The scatter (FIG. 6) and autofluorescence (FIG. 7) properties of the cells was determined on a FACScan™ flow cytometer at days 0, 4, 49 and 102. Comparing (A) through (D) with (E) through (H) in FIG. 6, it can be seen that there is no significant change in scatter with time for the reduced cells while there is a marked change for the non-reduced cells. The lymphocyte population for each scatter profile in FIG. 6 was estimated by the gates shown and the autofluorescence of the gated lymphocytes is shown in FIG. 7. Comparing (A) through (D) with (E) through (H), it can be seen that there is no significant change in autofluorescence with time for the reduced cells while there is a measurable change with time for the non-reduced cells.

To use the dried cells of the present invention as a standard in the calibration of or as a control for the calibration of the light scatter, compensation and/or fluorescence channels of a flow cytometer, cells prepared as in FIG. 5 may be used. The cells, if previously stained with FITC, PE or other fluorochromes (e.g., peridinin chlorophyll complex, allophycocyanin or Texas Red), would be rehydrated and run through the flow cytometer. Plots of light scatter and/or fluorescence such as those in FIGS. 5A through 5D would accompany the dried cells as part of a kit. If the cells were not previously stained prior to drying, the kit would contain the same plots as above but also would contain the cell markers. For immunofluorescence markers, there is no limitation on the invention of either the monoclonal antibody portion of the marker or the fluorescent portion. Any combination may be practiced in this invention.

The methods for adjusting the sensitivity of a flow cytometer will follow from the manufacturer's directions.

In another embodiment of the invention, cells which were fixed and reduced prior to freeze-drying in the presence of the protein, membrane stabilizing compound could be provided in a kit along with cell markers. The dried cells then would be handled in the same manner as the cells to be labelled in a sample. Staining profiles for the dried cells could be provided and a comparison made as a control. Any deviation from the profile would indicate that the tagging of the cells in the sample is suspect. These cells could be provided dried in a capillary tube, dried onto a slide or dried into some other container, such as a reagent vial, for use in cellular analysis.

In still another embodiment of the invention, cells which were fixed and reduced, whether labelled with cell markers or not, prior to freeze-drying in the presence of the protein, membrane stabilizing compound could be provided in a kit. The dried cells then would be used as a reference standard with which the cells in a sample could be compared. Again, these cells could be provided dried in a capillary tube, dried onto a slide or dried into some other container, such as a reagent vial, for use in cellular analysis.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed:

1. A dried mammalian cell useful as a reference particle in a immunoassay whose light scatter properties are substantially unaltered upon rehydration and whose autofluorescence does not increase with time wherein the cell has been fixed with a fixative, reduced with a Schiff's base reducing agent and then dried in the presence of a protein stabilizing compound.

2. The cell of claim 1 wherein the compound is selected from the group consisting of mono-, di- and polysaccharides.

3. The cell of claim 2 wherein the compound is a disaccharide.

4. The cell of claim 3 wherein the disaccharide is α-α-trehalose.

5. The cell of claim 1 wherein the cell is dried above the freezing point of water.

6. The cell of claim 1 wherein the cell is dried below the freezing point of water.

7. The cell of claim 1 wherein the cell is stained with at least one cell markers.

8. The cell of claim 7 wherein the cell is stained before drying.

9. Dried normal human peripheral blood leukocyte cells useful as reference particles in calibrating a flow cytometer, said cells having light scatter properties that are substantially unaltered upon rehydration and whose autofluorescence dose not increase with time, wherein said cells have been fixed with a fixative, reduced with a Schiff's base reducing agent, and then dried in the presence of a dissaccharide.

10. The cells of claim 9 wherein the cells comprise peripheral blood mononuclear cells.

11. The cells of claim 9 wherein the disaccharide is α-α-trehalose.

12. The cells of claim 9 wherein the cell is stained with at least one cell markers.

13. The cells of claim 12 wherein the marker is a fluorescently labelled monoclonal antibody.

14. The cells of claim 13 wherein the fluorescent label is fluorescein isothiocyanate.

15. The cells of claim 13 wherein the fluorescent label is r-phycoerythrin.

16. Dried normal human peripheral blood mononuclear cells useful as reference particles in calibrating light scatter and fluorescence channels in a flow cytometer, said cells having light scatter properties that are substantially unaltered upon rehydration and whose autofluorescence dose not increase with time, wherein said cells have been fixed with (para)formaldehyde, reduced with a Schiff's base reducing agent, and then dried in the presence of α-α-trehalose.

17. The cells of claim 16 wherein the concentration of trehalose is between 0.5% and 20% by weight.

18. The cells of claim 17 wherein the concentration is 5%.

* * * * *